United States Patent [19]

Wilhelm et al.

[11] Patent Number: 5,326,378
[45] Date of Patent: Jul. 5, 1994

[54] TRIS (2-ACETOACETOXY ETHYL)-AMINE, AND ITS HYDROSOLUBLE SALTS, PREPARATION PROCESS, USE AS FORMALDEHYDE COLLECTORS AND FINISHING PROCESS FOR FABRICS

[75] Inventors: Didier Wilhelm, Issy les Moulineaux; Antonio Gelabert, Bouffemont-Moiselles, both of France

[73] Assignee: Societe Francaise Hoechst, Puteaux, France

[21] Appl. No.: 80,825

[22] Filed: Jun. 24, 1993

[30] Foreign Application Priority Data

Jun. 25, 1992 [FR] France .................. 92 07798

[51] Int. Cl.$^5$ .................. D06M 13/322; C07C 69/72
[52] U.S. Cl. .................. 8/182; 560/178; 8/181
[58] Field of Search .................. 560/178; 8/181, 182

[56] References Cited

U.S. PATENT DOCUMENTS 4,127,382  11/1978  Perry .................. 8/181
5,051,529  9/1991  Witzeman et al. .................. 560/178

FOREIGN PATENT DOCUMENTS 0378067  8/1991  European Pat. Off. .
WO8809323  12/1988  PCT Int'l Appl. .

OTHER PUBLICATIONS

Nagoya Toryo KK, "Formaldehyde removal from amino resins—by reaction with active methylene cpds"; abstract, Section Ch, *Week* 7323, Dewrent Publication Ltd., London, GB; Class A, AN 73-33350U & JP-B-48 017 755, 1973.

C. Tomasino et al.: "Evaluation of Formalhyde Scvengers", pp. 33–38; Textile Chemists and Colorist, vol. 16, No. 12, 1984; Research Triangele Park.

*Primary Examiner*—Paul Lieberman
*Assistant Examiner*—Margaret Einsmann
*Attorney, Agent, or Firm*—Browdy and Neimark

[57] ABSTRACT

Tris(2-acetoacetoxy ethyl)-amine, and its hydrosoluble mineral or organic acid salts, preparation process, use as formaldehyde collectors, and finishing process for fabrics based on cellulose fibres.

5 Claims, No Drawings

TRIS (2-ACETOACETOXY ETHYL)-AMINE, AND ITS HYDROSOLUBLE SALTS, PREPARATION PROCESS, USE AS FORMALDEHYDE COLLECTORS AND FINISHING PROCESS FOR FABRICS

The present invention relates to tris (2-acetoacetoxy ethyl)-amine, its hydrosoluble mineral or organic acid salts, their preparation process, their use as formaldehyde collectors and a finishing process for fabrics.

Formaldehyde is widely used in the preparation of various aminoplastic resins, in particular for obtaining resins intended for finishing textile fibres such as urea-glyoxal-formaldehyde resins. In spite of the care taken in their preparation, these resins very often contain small traces of formaldehyde and, under certain conditions, in particular during their application to fabrics, they release the formaldehyde. Now, formaldehyde is a very penetrating, unpleasant, pungent-smelling gas; therefore very early on various methods were sought to fix it and/or to limit its release. Thus, various carbonylated compounds were proposed as a formaldehyde collector, possessing a methyl or methylene group in the alpha position such as acetaldehyde, acetone, acetylacetone, ether esters of acetylacetic acid and even more generally active methylene compounds such as nitroalkanes, dialkanol malonates (French Patent No. 989465 and 2575754, European Patent No. 2596, British Patent No. 2058099, Polish Patent No. 72885, Japanese Patent Application No. 73-17755, PCT Patent Patent Application No. WO88/09323 and C. TOMASINO et al, Textile Chemists and Colorists, 1984, 16, (12), 33-38).

However, these various products, although they are active, do not give total satisfaction according to a man skilled in the art.

Now, the Applicant has discovered with astonishment that tris (2-acetoacetoxy ethyl)-amine, and its hydrosoluble mineral or organic acid salts, have excellent properties for collecting the formaldehyde present in fabrics based on cellulose fibres finished with aminoplastic resins containing formaldehyde in the free or combined state.

This is why a subject of the present invention is tris (2-acetoacetoxy ethyl)-amine of formula (I):

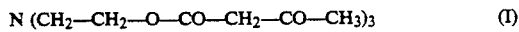

$$N(CH_2-CH_2-O-CO-CH_2-CO-CH_3)_3 \quad (I)$$

as well as its salts with hydrosoluble mineral or organic acids.

The mineral and organic acid salts of tris(2-acetoacetoxy ethyl)-amine soluble in water are the usual acid salts. Among the usual acids, there can be mentioned hydrochloric acid, nitric acid, sulphuric acid, orthophosphoric acid, phosphonic acid, phosphinic acid, paratoluenesulphonic acid, succinic acid, maleic acid, benzoic acid, citric acid.

According to the invention, tris(2-acetoacetoxy ethyl)-amine and its salts can be prepared by a process characterized in that 2,2,6-trimethyl 4-oxo 1,3-dioxine is reacted with triethanolamine, in order to obtain tris(2-acetoacetoxy ethyl)-amine which, if desired, is salified according to the usual methods.

Under the preferred conditions for implementing the invention, the condensation of 2,2,6-trimethyl 4-oxo 1,3-dioxine with triethanolamine is carried out:

at a temperature comprised between 55° and 150° C., with elimination of the acetone formed by distillation, in the presence of a solvent possessing a boiling point higher than that of acetone such as an aromatic hydrocarbon (benzene, toluene, xylene).

As has been said previously, tris(2-acetoacetoxy ethyl)-amine and its hydrosoluble mineral or organic acid salts have very useful properties as formaldehyde collectors, and in particular they allow the amount of free formaldehyde present in and/or released by fabrics based on cellulose fibres, finished with aminoplastic resins containing formaldehyde in the free or combined state, to be very considerably reduced.

For their use in the field of the finishing of fabrics based on cellulose fibres with aminoplastic resins currently used to give fabrics crease-resistance properties such as standard urea-glyoxal-formaldehyde resins, etherified or not with an alkanol such as methanol, tris(2-acetoacetoxy ethyl)-amine, or one of its hydrosoluble mineral or organic acid salts, is used in solution in the finishing bath, preferably at a dose of 0.001 to 2 moles per liter of finishing bath, and then the finishing is carried out under the usual conditions. After treatment, the fabrics thus finished contain practically no more free formaldehyde and/or formaldehyde which may be released.

This is why a subject of the present Application is also a finishing process for fabrics based on cellulose fibres using an aminoplastic resin containing formaldehyde in the free or combined state in which the fabrics are placed in a finishing bath, characterized in that tris(2-acetoacetoxy ethyl)-amine, or one of its hydrosoluble mineral or organic acid salts, is used in the said finishing bath as a formaldehyde collector.

The following examples are given for information only; they allow a better understanding of the invention but they do not limit its scope.

Except where indicated to the contrary, the parts and percentages are given by weight. The crease recovery test is carried out according to the AATCC 66-1972 standard, the crease recovery is expressed by the sum of the angles of crease recovery obtained in the direction of the warp and in the direction of the weft. The resistance to traction of the samples, expressed in daN, in the direction of the warp plus the direction of the weft, is carried out according to the AFNOR G 07.001 standard. The yellowing of the fabrics, carried out on a FIXOTEST apparatus at 185° C. for 30 seconds, and the whitness, expressed in degrees Berger, are measured with a spectrophotometer.

The amounts of formaldehyde, expressed in ppm, are determined according to the AATCC 112-1984 standard, designated hereafter AATCC 112.

EXAMPLE 1

The following are heated for two hours at 120° C. with concomitant distillation of the acetone formed:

251 mg of 85% 2,2,6-trimethyl 4-oxo 1,3-dioxine, that is 1.5 mole, 74.6 g (0.5 mole) of triethanolamine, 265 g of o-xylene, then about 220 g of o-xylene is eliminated under reduced pressure. The cooled reaction medium is then taken up in 400 g of distilled water. Decanting is carried out and the organic phase is washed twice with 400 g of distilled water. The extraction aqueous phases are united, then they are washed with 30 g of pentane, and finally, they are concentrated under reduced pressure. The residual oil is taken up in 530 g of dichloromethane, then the mixture obtained is dried over anhydrous magnesium sulphate, filtered and concentrated under reduced pressure. In this way 144.1 g of an orange-coloured oil is obtained, of which the NMR spectrum of the $^{13}C$ taken in solution in deuterized dimethylsulphoxide, conforms with tris(2-acetoacetoxy ethyl)-amine: NMR $^{13}C$ at 50 MHz (DMSO) δppm/TMS: 30 ($CH_3$), 49.6 (N—$CH_2$), 52.6 ($CH_2$), 63 ($CH_2$—O), 167.3 (COO), 201.5 (CO); NMR $^1H$ at 200 MHz (DMSOd$_6$) δppm/TMS: 2.17 (s, 9H, $CH_3$), 2.76 (t, 6H, d=5.7 Hz, N—$CH_2$), 3.54 (s, 6H, $CH_2$), 4.06 (t, 6H, J=5.7 Hz, O—$CH_2$).

Microanalysis for $C_{18} H_{27} NO_9$:401.41 Calculated C=53.86; H=6.78; N=3.49; O=35.87. Found C=53.4; H=6.9; N=3.5.

EXAMPLE 2

A 100% cotton poplin fabric, which has been scoured and bleached, weighing about 130 g per square meter with a 75% wring-out rate, is impregnated in a padding machine in an aqueous bath, the pH of which is indicated in table I, containing in solution:

55 g/l of a commercial resin sold by the Applicant under the name ARKOFIX®NFL Conc. which is a urea-glyoxal-formaldehyde resin weakly etherified with methanol, 15 g/l of a catalyst marketed by the Applicant under the name catalyst 3282, 2 g/l of a wetting agent: nonylphenol ethoxylated with 10 moles of ethylene oxide, 100 mmoles/l of tris(2-acetoacetoxy ethyl)-amine prepared in Example 1.

The fabric is then dried for 45 seconds at 120° C. then it is thermally treated for 35 seconds at 170° C. on a laboratory stenter.

The following are then determined on samples of the treated fabric:

crease recovery,
resistance to traction, hereafter called Rt,
whiteness, hereafter called Wh,
yellowing, hereafter called Ye,
the amount of free formaldehyde, expressed in ppm, hereafter called F,
resistance to chlorine The results obtained are given in table I as a comparison with a non-treated fabric (Example 3) and a fabric treated in the conventional way in the absence of a formaldehyde collector (Example 4).

Examination of table I permits the observation that the fabrics finished in the presence of tris(2-acetoacetoxy ethyl)-amine according to the present invention contain practically no more formaldehyde.

We claim:

TABLE I

| EXAMPLES | 2 | 3 | 4 |
|---|---|---|---|
| ARKOFIX NFL Conc (g/l) | 55 | 0 | 55 |
| Catalyst 3282 (g/l) | 15 | 0 | 15 |
| pH | 5.6 | | 4.1 |
| Crease recovery | 267 | 198 | 262.5 |
| Rt | 81.5 | 110.3 | 70.1 |
| Wh | 65.2 | 72.1 | 71.9 |
| Ye | 57.5 | 71.3 | 70.4 |
| F (ppm) | 1 | 0 | 203 |

1. Tris(2-acetoacetoxy ethyl)-amine or its hydrosoluble mineral or organic acid salts.

2. Preparation process for tris(2-acetoacetoxy ethyl)-amine, or its mineral or organic acid salts, characterized in that 2,2,6-trimethyl-oxo-1,3-dioxine is reacted with triethanolamine in order to obtain tris(2-acetoacetoxy ethyl)-amine which optionally is salified.

3. A process for finishing cellulose containing fibers which comprises placing the fibers in an aqueous finishing bath which contains an aminoplastic resin, the improvement comprising adding an effective amount of tris(2-acetoacetoxy ethyl)-amine or one of its hydrosoluble mineral or organic acid salts to act as a formaldehyde collector.

4. Process according to claim 3, characterized in that 0.001 to 2 moles of tris(2-acetoacetoxy ethyl)-amine, or one of its hydrosoluble mineral or organic acid salts, is used as the formaldehyde collector per liter of finishing bath.

5. A process for collecting formaldehyde which is present in cellulose containing fibers comprising applying to said fibers an effective amount of an aqueous solution of tris(2-acetoacetoxy ethyl)-amine or one of its hydrosoluble mineral or organic acid salts.

* * * * *